US010722622B2

(12) United States Patent
Loske

(10) Patent No.: US 10,722,622 B2
(45) Date of Patent: Jul. 28, 2020

(54) DRAINAGE SYSTEM AND VACUUM PUMP FOR INTRAUTERINE VACUUM THERAPY

(71) Applicant: LOHMANN & RAUSCHER GMBH & CO. KG, Neuwied (DE)

(72) Inventor: Gunnar Loske, Ahrensburg (DE)

(73) Assignee: LOHMANN & RAUSCHER GMBH & CO. KG, Neuwied (DE)

( * ) Notice: Subject to any disclaimer, the term of this patent is extended or adjusted under 35 U.S.C. 154(b) by 502 days.

(21) Appl. No.: 15/304,621

(22) PCT Filed: Apr. 10, 2015

(86) PCT No.: PCT/EP2015/000756
§ 371 (c)(1),
(2) Date: Oct. 17, 2016

(87) PCT Pub. No.: WO2015/158422
PCT Pub. Date: Oct. 22, 2015

(65) Prior Publication Data
US 2017/0035949 A1 Feb. 9, 2017

(30) Foreign Application Priority Data

Apr. 16, 2014 (DE) ........................ 10 2014 005 679

(51) Int. Cl.
A61M 1/00 (2006.01)
A61B 17/12 (2006.01)
(Continued)

(52) U.S. Cl.
CPC ........... A61M 1/0088 (2013.01); A61B 17/12 (2013.01); A61B 17/42 (2013.01); A61M 1/0037 (2013.01);
(Continued)

(58) Field of Classification Search
CPC .............. A61M 1/0088; A61M 1/0037; A61M 2210/1433; A61B 17/42; A61B 1/303;
(Continued)

(56) References Cited

U.S. PATENT DOCUMENTS 4,699,611 A * 10/1987 Bowden .................... A61F 2/04
604/105
4,895,559 A * 1/1990 Shippert .......... A61B 17/12022
604/15

(Continued)

FOREIGN PATENT DOCUMENTS

DE 10 2011 013743 A1 9/2012
DE 10 2012 023061 A1 6/2013
(Continued)

OTHER PUBLICATIONS

PCT Search Report dated Jul. 8, 2015 for priority PCT application, PCT/EP2015/000756. (the original Search Report is in German. We are supplying the original Search Report in German [3 pgs] and also an English translation [3 pgs].).

Primary Examiner — Adam Marcetich
Assistant Examiner — Jessica R Arble
(74) Attorney, Agent, or Firm — Stinson LLP

(57) ABSTRACT

A device for intrauterine vacuum therapy includes a pear-shaped fluid-collecting element and a fluid-communicating element. The fluid-collecting element defines an inlet opening at the proximal end and a tubular cavity for receiving a removable guide-rod during transvaginal insertion into a uterine cavity. The fluid-communicating element has a perforated distal end fixed within the fluid-collecting element outside the tubular cavity and has a proximal end adapted for connection to a vacuum-generating system. A method of treating an intrauterine wound or infection includes transvaginally inserting a drain into a uterine cavity and applying (Continued)

a negative pressure to the drain such that the uterus collapses and the inner wall is aspirated against the drain.

23 Claims, 16 Drawing Sheets

(51) Int. Cl.
    *A61B 17/42*     (2006.01)
    *A61B 1/012*     (2006.01)
    *A61B 1/303*     (2006.01)

(52) U.S. Cl.
    CPC ............... *A61B 1/012* (2013.01); *A61B 1/303* (2013.01); *A61B 2017/12004* (2013.01); *A61B 2017/4216* (2013.01); *A61B 2217/005* (2013.01); *A61M 2210/1433* (2013.01)

(58) Field of Classification Search
    CPC ............ A61B 1/012; A61B 2017/4216; A61B 2217/005
    See application file for complete search history.

(56) References Cited

U.S. PATENT DOCUMENTS

| | | | |
|---|---|---|---|
| 6,068,477 A * | 5/2000 | Mahlmann | A61C 17/08 433/96 |
| 6,264,671 B1 * | 7/2001 | Stack | A61F 2/95 606/191 |
| 8,550,088 B1 * | 10/2013 | Booher, Sr. | A61B 17/4241 128/846 |
| 2006/0163097 A1 * | 7/2006 | Murray | A61M 25/0009 206/364 |
| 2010/0056910 A1 * | 3/2010 | Yanuma | A61M 25/09041 600/434 |
| 2010/0179493 A1 | 7/2010 | Heagle et al. | |
| 2011/0015586 A1 * | 1/2011 | Orgill | A61F 13/0216 604/290 |
| 2013/0245581 A1 | 9/2013 | Norred et al. | |
| 2013/0245637 A1 * | 9/2013 | Norred | A61B 17/42 606/119 |
| 2015/0148785 A1 * | 5/2015 | Kleiner | A61M 1/0088 604/543 |

FOREIGN PATENT DOCUMENTS

| | | |
|---|---|---|
| DE | 10 2012 003129 A1 | 8/2013 |
| WO | WO 2012/123414 A1 | 9/2012 |

* cited by examiner

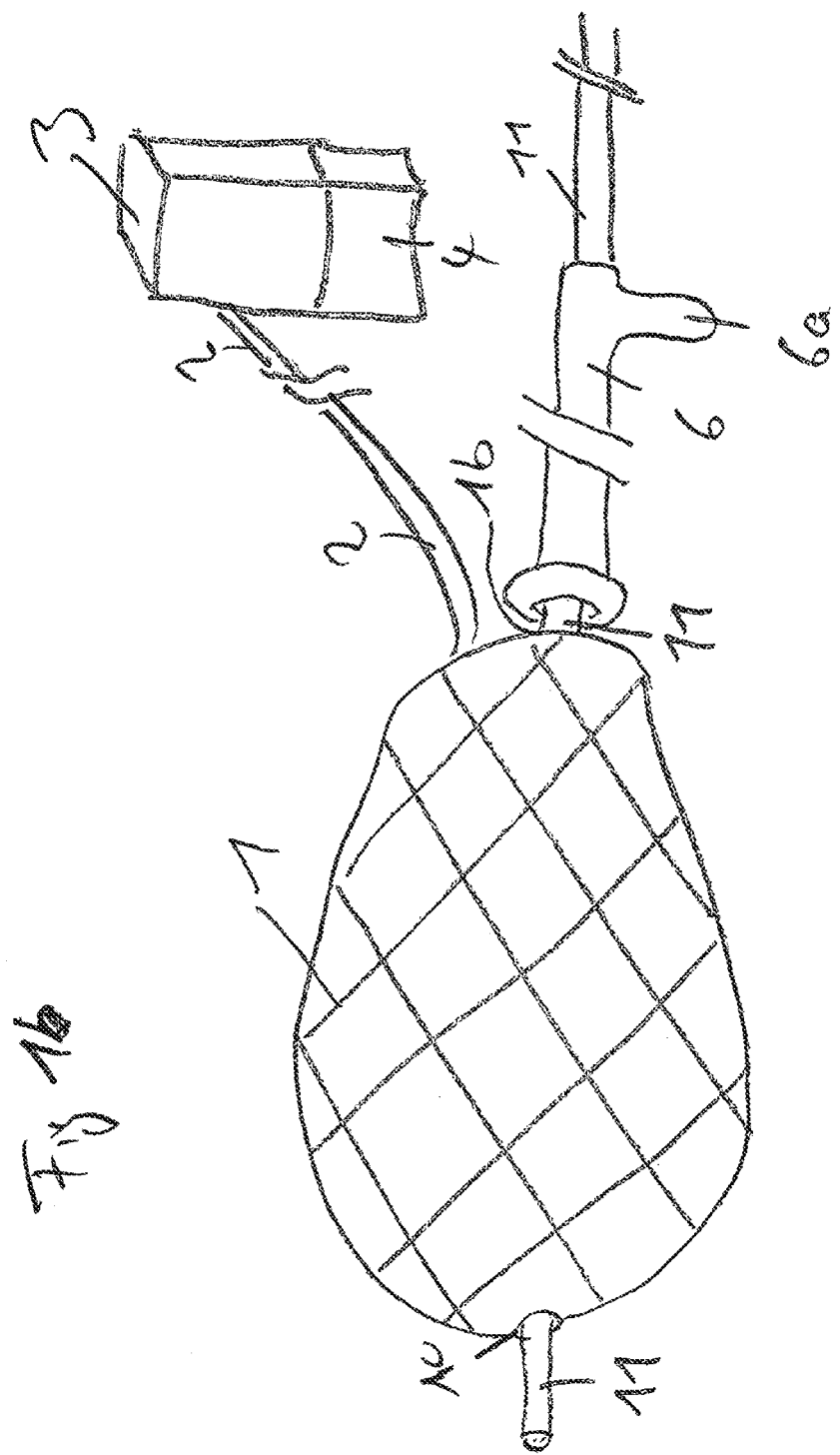

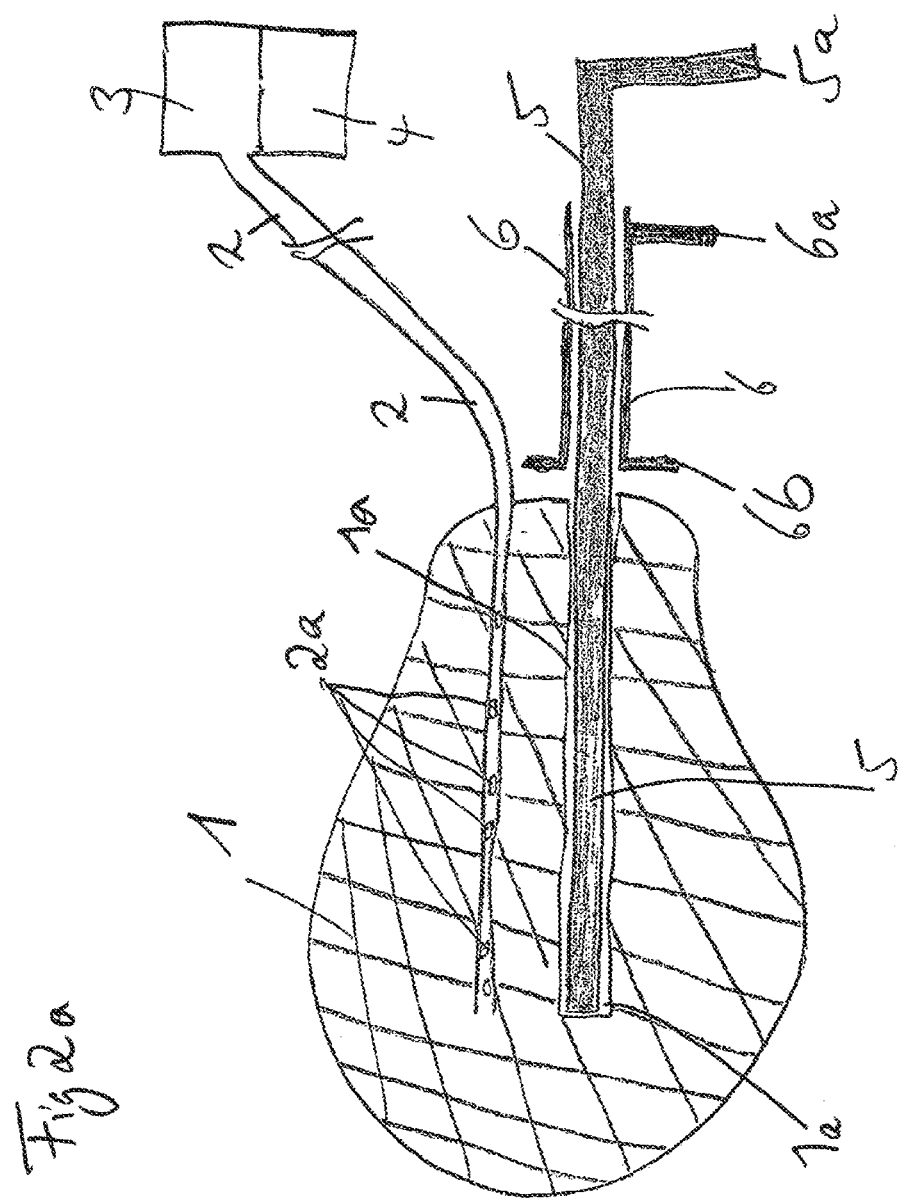

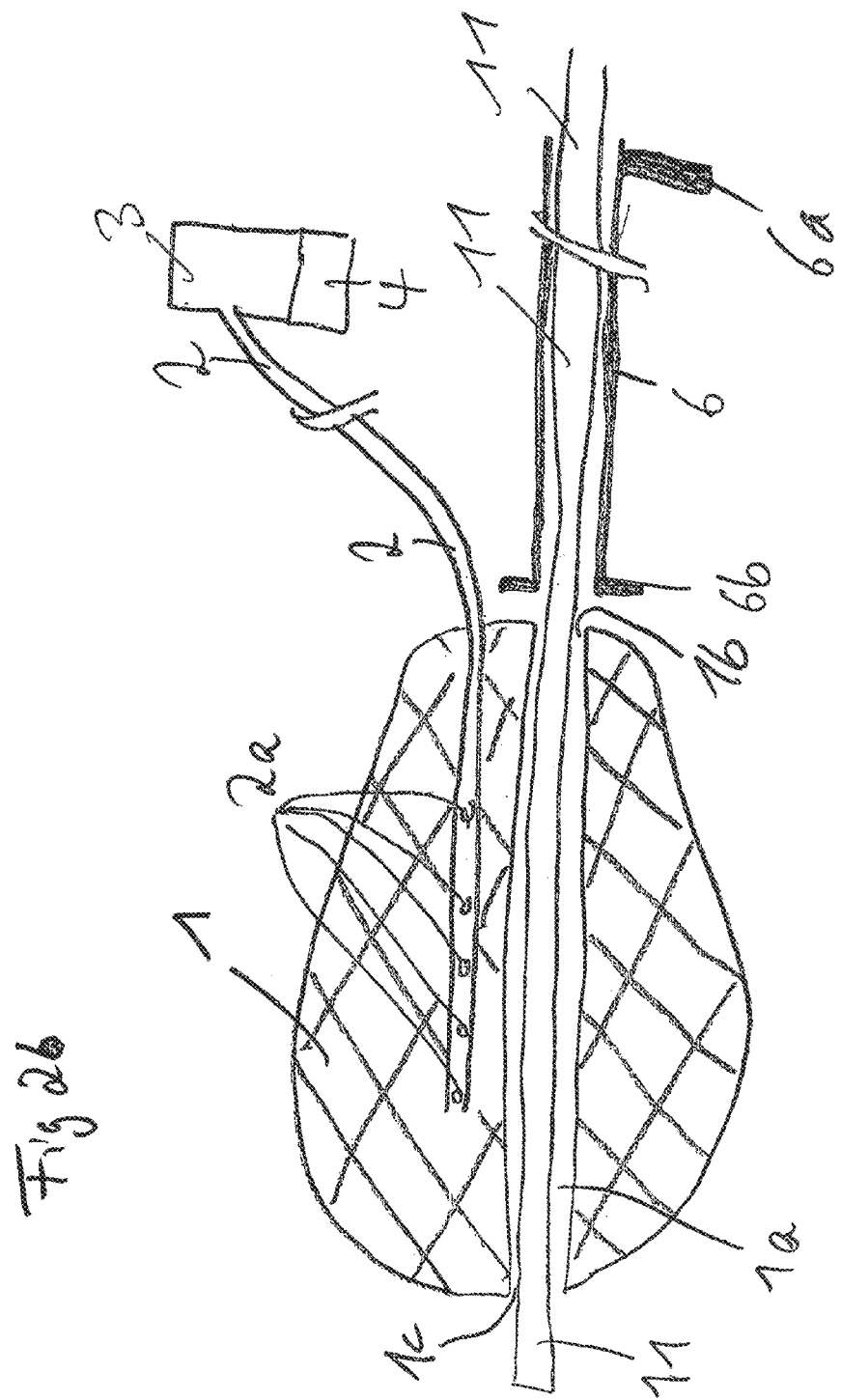

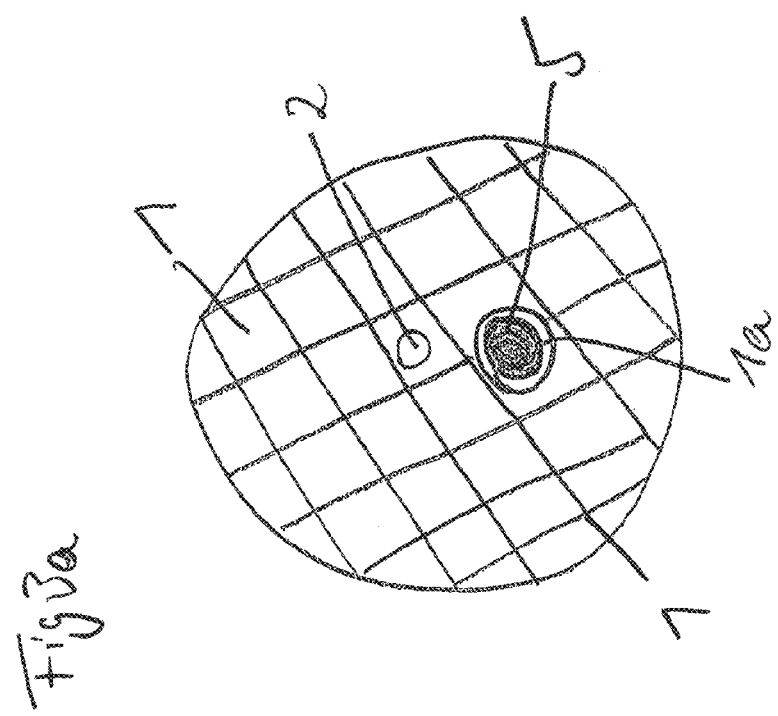

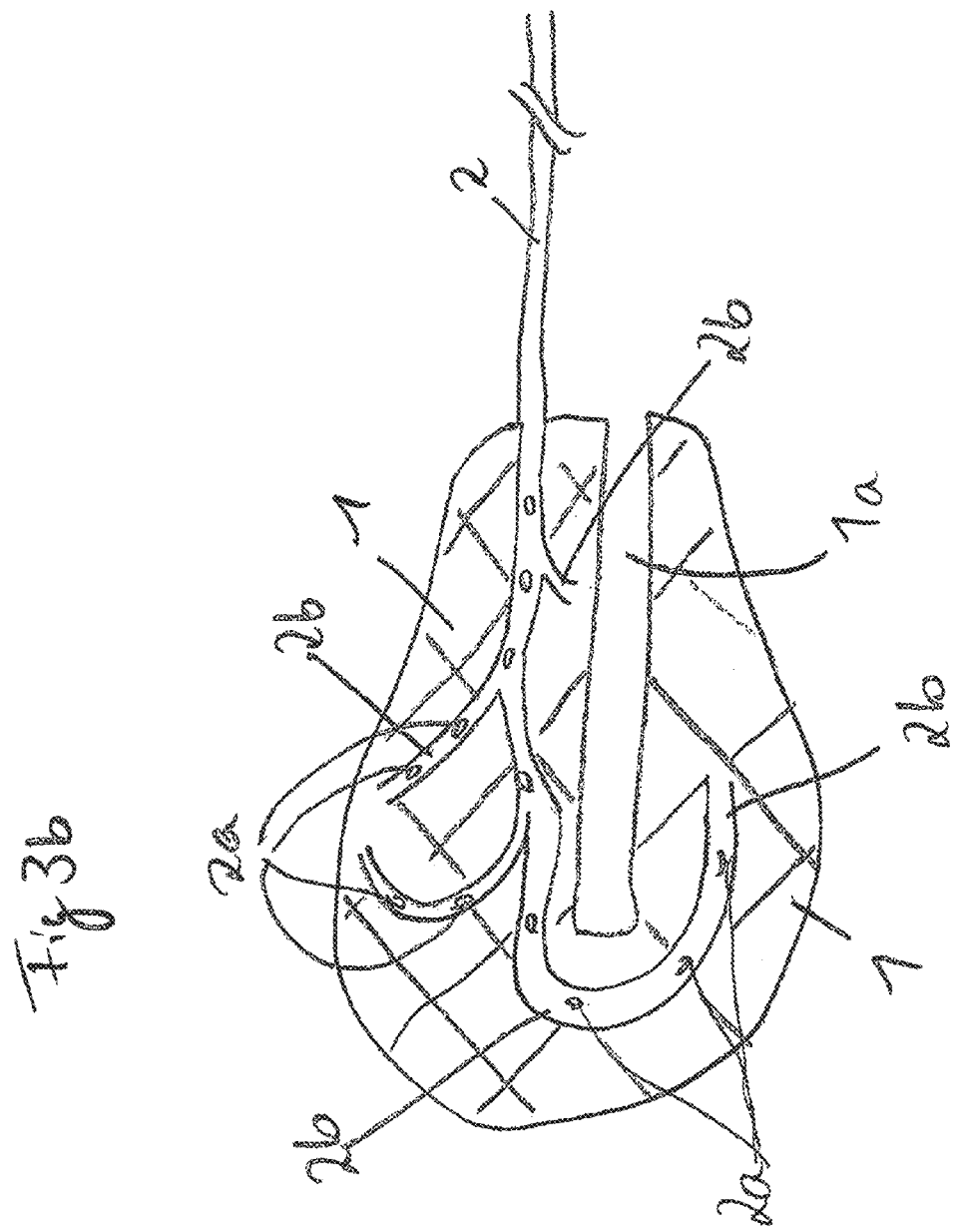

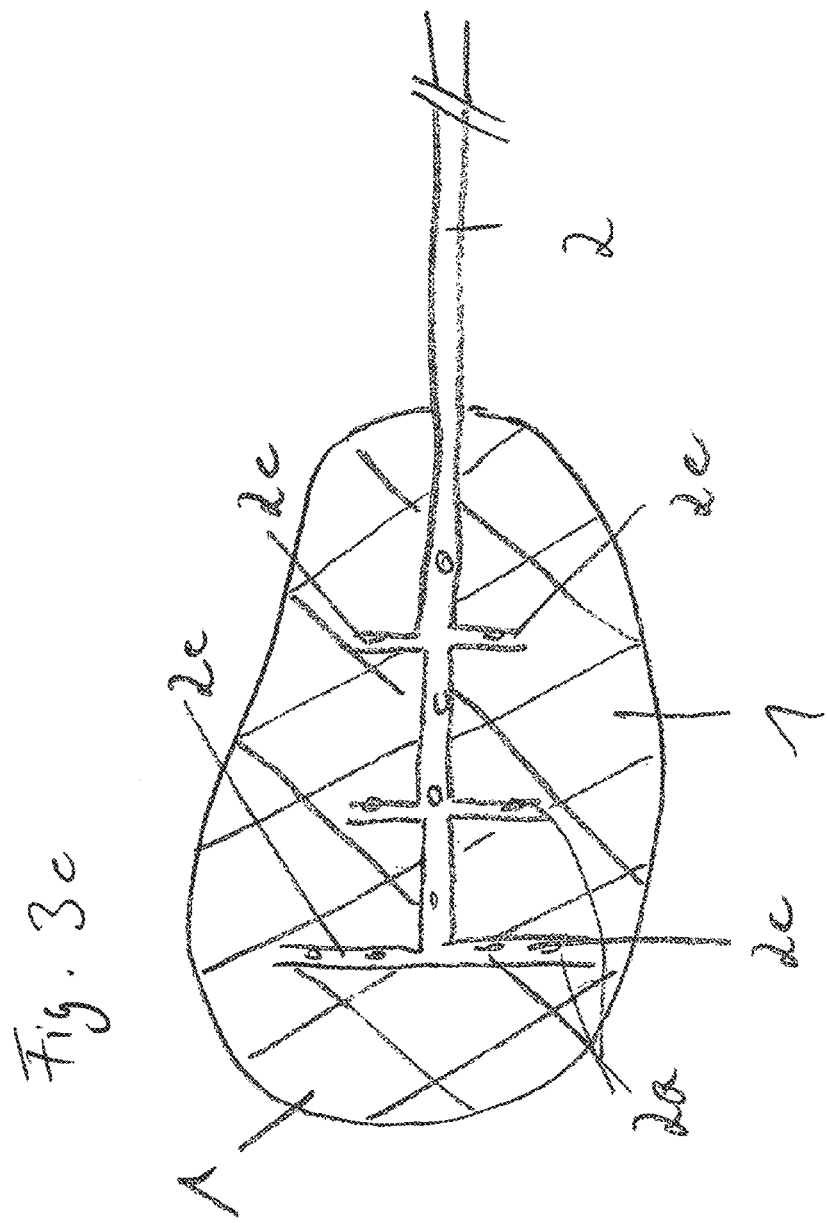

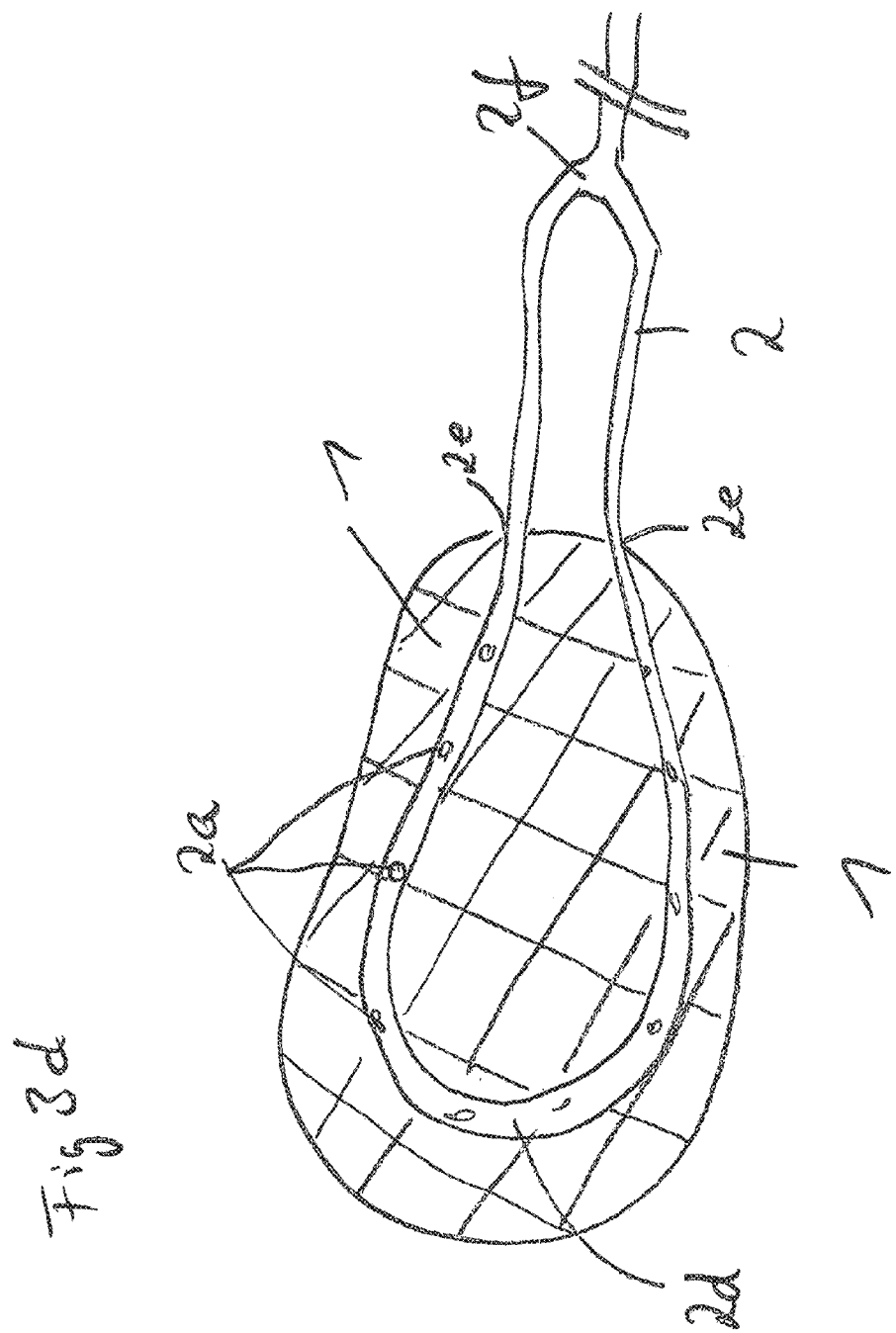

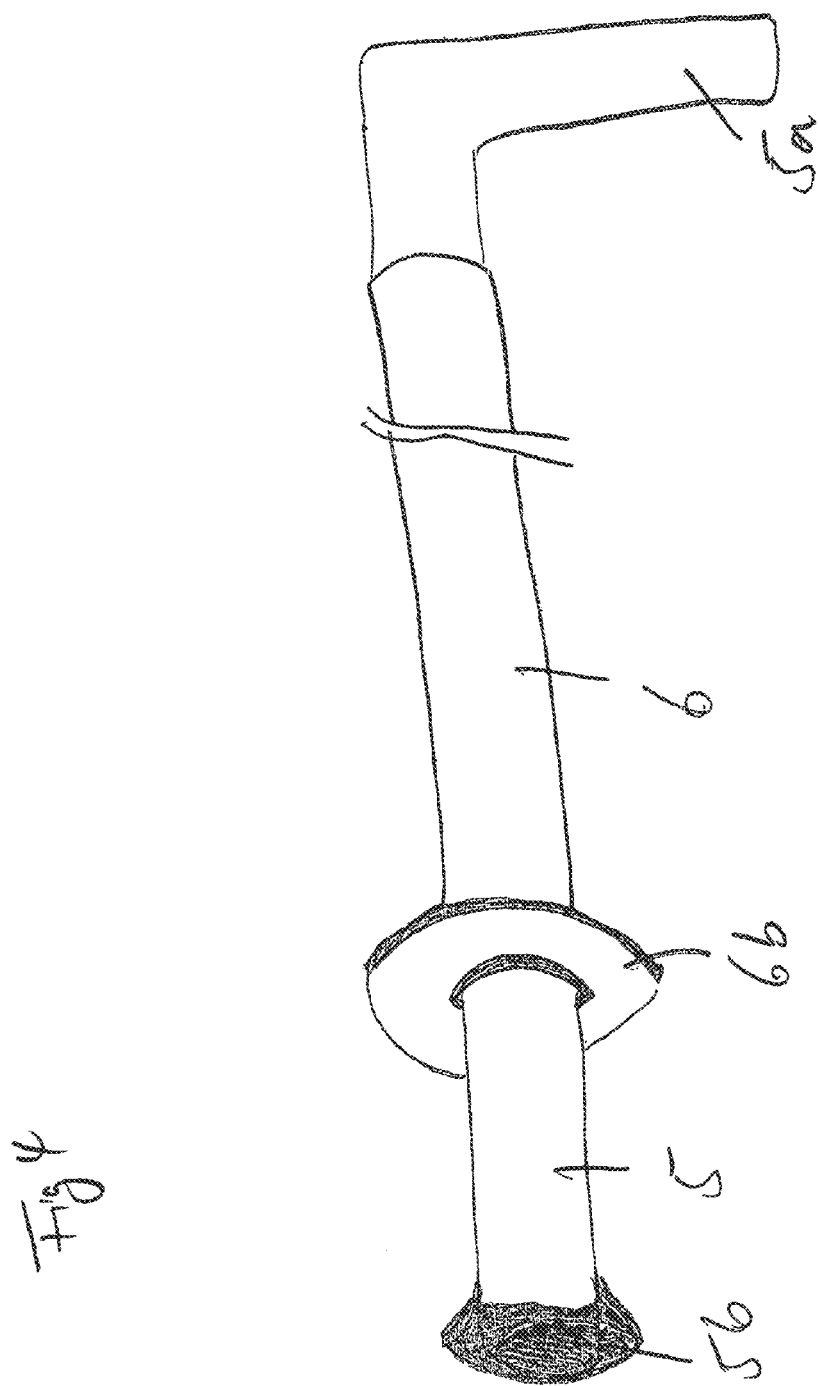

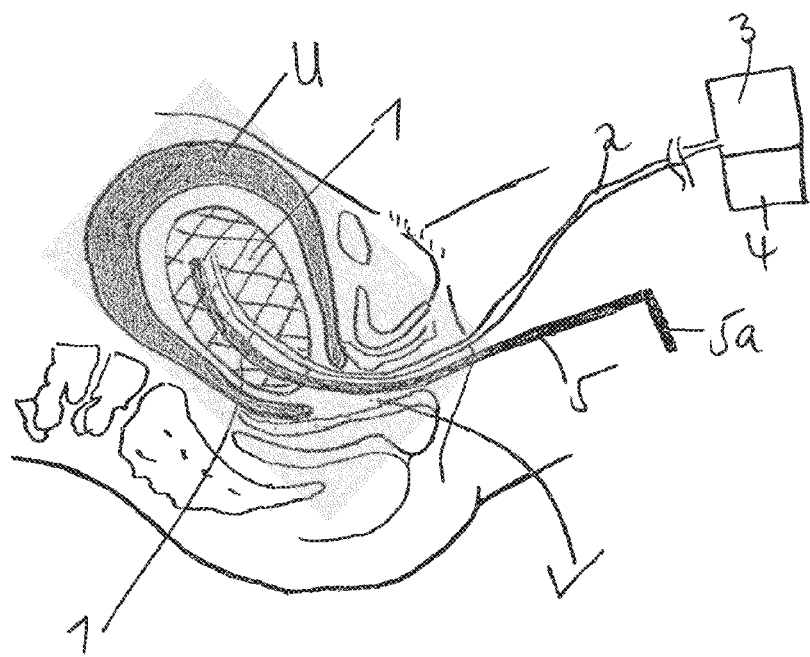

DRAINAGE SYSTEM AND VACUUM PUMP FOR INTRAUTERINE VACUUM THERAPY

CROSS-REFERENCE TO RELATED APPLICATIONS

This is a national phase application from PCT Patent Application Serial No. PCT/EP2015/000756 filed on Apr. 10, 2015, which claims priority to German Patent Application Serial No. 10 2014 005 679.1 filed on Apr. 16, 2014, each of which is incorporated herein by reference in its entirety.

STATEMENT REGARDING FEDERALLY SPONSORED RESEARCH OR DEVELOPMENT

Not applicable.

BACKGROUND OF THE INVENTION

Negative pressure therapy (vacuum therapy, vacuum sponge therapy, low pressure therapy) is used for treatments of external wounds. An open-cell polyurethane foam or another open-cell wound filler (e.g. cotton gauze) is inserted into the wound and occluded using a film. Subsequently, a vacuum is applied to this dressing using a vacuum-generating system (for example an electronic vacuum pump). In this way, wound secretion and wound edema can be permanently drained over several days, and infected wounds can be cleansed. Blood circulation is improved, granulation is stimulated. The objective is to provide the conditions for a stable secondary wound situation, subject to which the wound can continue to heal. The open-cell wound fillers can be antimicrobially treated. In addition to occlusion, the dressing can also be flushed under controlled conditions. For this purpose, special pumps are used, which can both aspirate and irrigate using a flushing solution.

The treatment principle is also applied endoscopically, for example for the treatment of anastomotic leaks on the rectum or internally on the esophagus.

The treatment is also used intra-abdominally for the treatment of peritoneal inflammation. For this purpose, special open-cell films, to which a vacuum can be applied, are also used. There are also special wound dressing bandages, to which a vacuum can be applied.

No special vacuum bandage systems or drains exist, which are suitable for intrauterine therapy. No intrauterine vacuum therapy treatment applications have been published or otherwise scientifically described.

BRIEF SUMMARY OF THE INVENTION

The invention relates to a drain and electronic vacuum pump, which can be used intrauterine for vacuum therapy.

Hereinafter, the prerequisites and clinical problem presentations are described, from which the embodiments, on which the invention is based, are derived.

Atonic Uterus, Uterine Postpartum Bleeding

During a pregnancy, both the strong muscular wall of the uterus, the placenta, and the uterine cavity, in which the baby and the placenta are located, grow. After childbirth, the afterbirth detaches from the uterine cavity, and a large intrauterine wound surface develops. In a normal situation, the blood vessels of this wound surface close as a result of the contraction of the uterus, accompanied by hormonal effects, and birth bleeding ceases.

If the uterus is unable to contract, a so-called atony accompanied by severe bleeding complications and even exsanguination of the patient can occur. The conservative therapies consist of manual compression and medicinal, hormonal stimulation for contraction of the uterus. The goal is to incite the muscles of the uterus to self-contract. If the therapy fails and bleeding persists, as a last resort, the emergency surgical removal of the bleeding uterus must take place to save the mother's life.

Endometritis, Infections after Childbirth, Abortion or Pregnancy Termination

A pregnancy can cause an infection of the amniotic cavity accompanied by an infection in the amniotic fluid, the placenta and the baby. The baby may die in the uterus. Via the uterine cavity, germs and endotoxins may be washed into the mother's circulatory system and cause the mother's systemic infection. Locally, intrauterine, an inflammation of the endometrium or endometritis exists.

With each abortion and after any pregnancy termination, an infection of the patient originating in the inner wound surface of the uterus may occur. The treatment consists in antimicrobial therapy and curettage. Furthermore, a transmural injury to the uterine wall may occur (iatrogenic or during childbirth).

In summary, two major problems, to which the principles of vacuum therapy might be applied, may occur during pregnancy: intrauterine bleeding and infection.

Fluid-Communicating Element

An open-cell fluid-collecting element is fluid-conductively connected to at least one fluid-communicating element. Fluids and/or gases may be conducted. The fluid-communicating element consists of a drainage tube, whose distal end is permanently connected, via fluid conducting perforations, to the fluid-collecting element. Fastening takes place via sutures and/or gluing and/or another fastening method. The fluid-communicating element is situated in the longitudinal axis or parallel to the longitudinal axis. Within the fluid-collecting element, the fluid-communicating element is provided with a multiplicity of branch-like branches, which may lead to any place in the collecting element. The branches are T-like pieces. In particular, the fluid-communicating element extends loop-like in the fluid-collecting element. It enters at the proximal end, passes through the body in a loop and exits at the proximal end. The entering and exiting fluid-communicating element can advantageously be fluid-conductively combined with one another in a y-shape. The branched and/or loop-like and/or meandering and/or arching and/or spirally extending fluid-communicating elements branched in the fluid-collecting element entail the advantage that, just as a result of the orientation, sufficient fixation in the fluid-collecting element exists and no additional suture or glu-ing is necessary. The fluid-communicating element per se may have different lumens. Using the ramifications, it can be conducted all the way to the surface of the fluid-collecting element and can also be used for flushing the surface and/or the body.

Its proximal end is connected to a vacuum-generating system. This system consists in particular of a vacuum pump, by means of which a negative pressure between 20 and 200 mm Hg can be generated. The tube is vacuum-stable. It is preferably transparent. It preferably has a diameter between 2 mm and 20 mm and a length of 30 cm to 120 cm.

Fluid Collecting Element

The fluid-collecting element preferably consists of an open-cell polyurethane foam body. It consists of a different material, which has fluid-collecting open-cell properties. It consists of one and/or more plastics. It consists of a combination of different open-cell materials. In particular, it consists of an open-cell foam and an open-cell film. Preferably, the cells are situated close to each other, as close as in a sponge body. The cell size is preferably between 100 μm and 2000 μm.

The fluid-collecting element may have any body shape. Preferably, the body shape is pear-shaped, modeled on the uterus. The body shape is preferably a cylindrical shape. The body shape is preferably egg-shaped. The size of the body is adapted to the size of the uterine lumen depending on the progress of the pregnancy. It is available in several graduated adapted sizes. The transverse diameter of the body in the transverse axis preferably measures from 1 cm to 15 cm. The length of the body in the longitudinal axis is preferably 2 cm to 30 cm. The fluid-collecting element can be customized in size. The fluid-collecting element should be dimensioned in such a way that it can be fully introduced into the uterus.

The invention is applied in utero. Transvaginally, the fluid-collecting element is introduced into the uterine cavity via the opened cervix. For this purpose, the cervix can be dilated if necessary. After a childbirth, the cervix is open and, as a result, sufficiently wide. Dilation is then unnecessary. After intrauterine placement, a vacuum is applied to the fluid-communicating element. The uterus collapses subject to the suction and aspirated to the fluid-collecting element.

This is intended to mechanically stimulate the self-contraction of the uterus, which fails during atony. As a result of the applied vacuum, contraction of the uterus is induced and the body's own hemostatic mechanisms are provided support. If a negative pressure is applied to the fluid-collecting element, the inner wall of the uterus attaches itself to the open-cell surface of the fluid-collecting element and is aspirated. The cervix, across which an outward connection via the vagina exists and from where air could be aspirated, also attaches itself to the fluid-collecting body. As a result of the aspiration of the tissue, a compartment is formed, in which the negative pressure can be generated.

If the fluid-collecting element still protrudes into the vagina, air from outside can be aspirated through the introitus vaginae and prevent the generation of suction buildup in the uterus. Sealing of the vagina can additionally be achieved using a pessary, which is conducted via a perforation across the drainage tube or using a different vaginal closure by means of a non-fluid-conducting vaginal tamponade. It is seated in the vagina quasi like a cork and seals it against the fluid-collecting element.

At the proximal end, the fluid-collecting element can also not be equipped fluid-conductive, in order to provide a better seal against the vagina in a vaginal placement. The wall of the fluid-communicating element can also be distended piston-like at its exit location at the fluid-collecting element and can contribute to the sealing of the vagina quasi like a stopper or cork so that no air is aspirated.

During vacuum therapy, using the negative pressure, both a suction force, which faces away from the wound surface, and, using the aspirated fluid-collecting element, a compressive force, is also exerted, which faces the wound surface. The compressive force on a wound surface depends on the level of the negative pressure. It also depends on the rate of filling of the wound with the collecting element and on the compressibility of the fluid-collecting element. The more the lumen of the intrauterine cavity is filled by the fluid-collecting element, the more of the inner wound surface is in contact with the fluid-collecting element. An inner tamponade can be made using the fluid-collecting element and subsequently the negative pressure can be additionally applied. A plurality of single fluid-collecting elements can also be inserted. These additional elements need not be individually equipped with a fluid-communicating element. As a result of the open-cell surface, for vacuum generation on the element it is sufficient if its surface is in direct fluid-conducting contact with another element, to which a vacuum can be applied. The more the inner lumen is tamponed with the fluid-collecting element, the greater the internal wound surface, which is directly exposed to the suction. If an obviously small-volume fluid-collecting element is placed into the uterine cavity, direct contact with the fluid-collecting element is less. The less compressible the fluid-collecting element is, the more pressure is exerted on the aspirated wound surface during vacuum development.

This effect of mechanical pressure exertion is used for hemostatis in intrauterine vacuum therapy. On the one hand, the uterine wall is pulled to the fluid-collecting element and contracts during this process around the fluid-collecting element, on the other hand, the negative pressure exerts mechanical pressure from the inside on the uterine wall. The higher the negative pressure that is applied, the higher is also the compressive effect on the inner wall. The more the cavity is tamponed, the higher the compressive effect on the inner wall.

The open-cell fluid collection body may be of soft or firm consistency, it may be compressed subject to a negative pressure. It may maintain its shape subject to a vacuum and be vacuum-stable. The extent of vacuum stability can be expressed as a percentage of the original body. 100% vacuum stability means: the body does not become deformed subject to the negative pressure. 50% vacuum stability means: subject to negative pressure, the body shrinks by half, and so on. The vacuum stability data are intended to apply to an applied vacuum of −20 mm Hg to −200 mmHg. Similarly, the vacuum stability can also be expressed by the compressibility value.

The more compression-resistant the fluid-collecting element is, the higher is the compressive effect on the inner wall. In case of an internal tamponade, additional compression can be exerted surgically or through the abdominal wall using external pressure and contribute to the hemostatis. In particular, for the fluid-collecting element, compression stability of 10%-90% of its initial volume should exist for suction between 20 mm Hg and 200 mmHg. This means that at such a negative pressure, the volume of the fluid-collecting element is reduced to 10%-90% of its original volume.

The fluid-collecting element serves as a medication carrier. In particular, the fluid collection element is equipped with hemostatic medications. The hemostatic medications are applied to the surface of the fluid-collecting element and come into direct contact with the inner wound surface. The hemostatic medications may be of a mineral nature. They may be applied to the fluid-collecting element in the form of powders and/or fluids and/or foams and/or gauzes and/or ointments. They may be also sprayed into the cavity as a powder before placement of the fluid-collecting element. In particular, the hemostatic medications can be endoscopically introduced into the uterine cavity before placement of the fluid-collecting element.

The medications may be introduced via the work channel of an endoscope. They may be flushed in or sprayed. They may be blown in using excess pressure.

Via additional fluid and/or gas conducting communication elements, which are preferably tubular and situated in the fluid-collecting element, they can be introduced into the uterine cavity. In particular, the medications should be introduced in a targeted manner via an open-cell and/or a one-sided open-cell film, by which the fluid-collecting element is enveloped and which is the surface of the fluid collection element body. The open-cell or one-sided open-cell film that lies at the surface is provided with at least one additional fluid-communicating element, via which medications can be delivered. The utilization of the film as medication carrier or to supply medium has the advantage that the medication is distributed only on and/or within the film. In this way, the medication can be applied to the inner wound surface in a targeted manner. The hemostatic medications may consist of enzymes, minerals, coagulation factors, hormones. In particular, the medications may consist of zeolites, microporous crystalline aluminosilicate or chitin and/or chitosan-biopolymers or smectite aluminum silicate or kaolin aluminum silicate or plasma protein.

Guide Rod and Sheath

The fluid-collecting element is placed transvaginally using a guide-rod. The guide-rod consists of metal or plastic. It is 20 cm-120 cm long. It has a diameter of 2 mm-25 mm. Its proximal end is equipped with a handle. At its distal end, it ends obtuse or rounded. The distal end is formed flared stamp-like. In particular, the distal end of the guide-rod is softly kinkable and/or flexible and atraumatically constructed. The guide-rod is adapted to the natural course of the birth canal and the uterus and is curved.

The guide-rod is introduced into the fluid-collecting element. The fluid-collecting element has a cylindrical tubular cavity for receiving the guide-rod in the longitudinal axis or parallel to the longitudinal axis. The diameter of the cavity corresponds to the diameter of the rod. The diameter of the cavity is slightly smaller than the diameter of the rod so that it can be wedged into the cavity and is thereby fixed. The tubular cavity terminates in a blind end in the fluid-collecting element. The guide-rod will be introduced up to this end.

The cylindrical recess for receiving the guide-rod can consist of a tube integrated in the fluid-collecting element. The tube may have a blind closure at its distal end. The tube may extend over the entire longitudinal axis of the fluid-collecting element and be open on both sides. The tube can be made of plastic. The tube is funnel-shaped at its proximal end and terminates flush with the fluid-collecting element or projects beyond it. The tube may be fluid-conductively perforated.

The tube or the tubular cavity terminates at the distal end within the fluid-collecting element. In this situation, the risk of perforation of the uterus during the advance of the fluid-collecting element is reduced.

The tubular cavity extends through the entire longitudinal axis of the fluid-collecting element, at the proximal end of the fluid-collecting element, it has an inlet opening and at the distal end an outlet opening. In this case, the fluid-collection element can be pushed back and forth on the guide-rod. For placement of the fluid-collecting element, the guide-rod is first transvaginally inserted into the uterine cavity, and then the collecting element located on the guide-rod is pushed into the uterine cavity in a distal transvaginal direction.

Suction is applied and the guide-rod is removed. The center portion of the guide-rod may be provided with a disc-like attachment. When the rod has been inserted into the fluid element, the proximal end of the fluid-collecting element is adjacent to the disc-like attachment, so that during the push forward, both the distal end of the rod and the disc-like boundary are pushed as well. The disc-like attachment may be pushed in a distal direction on the rod. It is connected to an additional push rod, which is integrated in the guide-rod and can be pushed back and forth in a longitudinal slot of the guide-rod. During the retraction maneuver of the guide-rod, i.e., during removal from the fluid-collecting element, the disc-like attachment can be simultaneously pushed forward, so that the fluid-collecting element remains in position upon removal of the guide-rod.

The guide-rod is equipped with a pusher sheath, which is also made of metal or plastic (is guided). The pusher is a tube with openings at the distal and the proximal end. The sheath has a slightly larger diameter than the rod. At the distal end, the sheath is shaped stamp-like. Preferably, the distal end is closed by a disc for pushing the fluid-collecting element. The distal end of the sheath is shaped like a funnel. The sheath is intended to push the proximal end of the fluid-collecting element ahead of itself for placement. The sheath is displaceable on the guide-rod. Using the sheath that is displaceable on the guide-rod, the fluid-collecting element is displaced in a distal direction for placement. When the rod is removed, the sheath fixes the fluid-collecting element in the placement position. The sheath can be applied both in the case of a tubular cavity that terminates in a blind end in the fluid-collecting element and in a cavity that is open on both sides. The sheath has a transverse diameter of 3 mm to 25 mm. The disc-like closure has a diameter of up to 5 cm. The sheath is 20 cm to 80 cm long. The proximal end of the sheath has a guide handle.

In particular, an endoscope should be used as a guide-rod. The pusher can be moved on the endoscope on the longitudinal axis and slide. Via the working channel of the endoscope, hemostatic medications can be administered prior to placement of the drain locally in the wound cavity. Conventional gastroscopes and coloscopes are used as guide-rods.

Vacuum Pump

In contrast to the vacuum therapy in infected wounds, the intrauterine vacuum therapy during uterine atony is primarily designed for a short-term therapy duration of a few minutes or a few hours. It may be interrupted and resumed as required.

The negative pressure for intrauterine therapy is in particular generated by an electronic vacuum pump. The pump is fluid-conductively equipped with at least one secretion collection vessel. The collection vessel preferably has a volume of 100-1000 mL.

The vacuum application can take place continuously and intermittently. The vacuum pump can generate specific suction patterns. For this purpose, the pump is equipped with a controller, which can be operated via a display screen. Using pressure sensors, the pump continuously measures the negative pressure values in the vacuum-conducting system and is fluid-conductively connected to the fluid-communicating element. The negative pressure can also be fed back to the control element via electronic sensors, which are integrated in the fluid-communicating element or the fluid-collecting element. Via the control element, the pump permanently regulates the vacuum automatically, as specified in the default settings of the control unit.

The self-contraction pattern of the uterus can also be fed back to the control unit. The suction pattern of the pump can be adapted to the self-contraction pattern of the uterus and reinforce it. For this purpose, direct electronic and/or electromyographic and/or tonic derivations of the uterus can be derived via measuring sensors, which are fed to the control element. The contractions of the uterus wall can be derived via contact electrodes which are in contact with the wall inside or outside. The adaptation to the self-contraction pattern takes place automatically. The vacuum tamponade acts in this manner like a mechanical pacemaker of the uterus and supports and reinforces the self-contraction capacity. The vacuum pattern can be synchronized with the contraction of the uterus.

Using the controller, the vacuum values can be individually adjusted. The duration of the negative pressure and the negative pressure pauses can be controlled. The minimum negative pressure and the maximum negative pressure, as well as gradations between the values, can be adjusted. The ascent and descent profile and/or the speed of the vacuum generation can be adjusted. It is possible to set individual pressure profiles. In particular, using an electronically controlled vacuum pump, uterine contraction-like suction patterns can be generated, which mimic the natural contractions of the uterus. In particular, the uterine contraction-like suction profile has an active negative pressure phase with suction durations of 10 s to 120 s and a suction disruption pause duration of 10 s-120 s. In particular, the suction profile can fluctuate between a base negative pressure and a peak negative pressure. It may, in particular, fluctuate undulating around a medium negative pressure. The basic negative pressure may correspond to a complete suction drop to 0 mm Hg.

In particular, the base negative pressure should not correspond to a vacuum of 0 mmHg but be continuously lower than 0 mmHg, so that a permanent negative pressure remains applied to the inner wound surface during therapy. In addition, to this permanent base negative pressure, a supplementary negative pressure in the form of contractions and/or in the form of sinus curves and/or saw blade shape and/or undulating wave form with or without pauses should be applied. Even with a fluctuating pressure profile, a negative pressure should always be applied to the inner wound surface. This base negative pressure should preferably be between −5 and −100 mmHg. This negative pressure profile intends to imitate a permanent postpartum contraction of the uterus with supplemental reinforcing labor-like uterine contractions, which are required for hemostasis. The supplemental labor-like postpartum uterine contractions, during continuous permanent suction, using the pump, can also be conducted to the uterine muscles via hormonal medications and electrical pacemaker impulses.

The contraction patterns are transmitted to the walls of the uterus by the suction. In particular, the contraction pattern extends in wave-form. In particular, it follows the bell-shaped course of a sinus curve.

The pump is intended to produce a sawtooth-like contraction pattern. After a suction drop at a dead volume of 100 mL-1000 mL, the pump is intended for generating the maximum peak negative pressure during a rapid time interval of less than 2 s. In particular, in the case of a dead volume of 200 mL to 500 mL, it should be possible to generate the peak negative pressure in less than 2 s. The pressure drop to the base negative pressure should be achievable over a longer interval. This interval should last between 10 s and 120 s. Inversely, it should also be possible for suction to rise gradually over a time interval of 10 s to 120 s and drop to the base value rapidly within 2 s to 5 s.

In particular, it should be possible to generate the negative pressure over a period of 10 s to 120 s. The pressure curve course can be individually adjusted. Both the base negative pressure values, below which the negative pressure should not drop, and the chronological developments with duration of base pressure and/or peak pressure and/or gradations in the pressure curve and/or speed of the vacuum build-up and/or degradation and/or the duration of the pressure plateaus and/or pauses can be individually determined and adjusted using the input module of the pump.

The vacuum therapy during atony of the uterus is used primarily to overcome the atony of the uterus and, using the inner negative pressure, to actively cause contractions of the uterus by mechanical means and thereby inducing or supporting the natural hemostasis. Once soon as this mechanism was activated, early removal of the fluid-collecting element is also possible. In contrast to this short-term therapy, vacuum therapy is used for the treatment of infected wounds over several days and is changed several times at intervals of several days. The vacuum therapy during atony can also be used over an extended period of time of days, in which case the sponge size is continuously reduced during the changeover and adapted to the size of the uterine lumen. During atony, the vacuum therapy is used as an emergency measure with an entirely new therapeutic approach to uterine contractions.

The vacuum therapy can also be implemented in case of uterine infections. In particular, vacuum therapy is usable for the treatment of postpartal endometritis, after an abortion or a pregnancy termination.

The above-described embodiments of the invention are equally suitable for this purpose. The therapy is not carried out in the short term over hours but instead over several days. The drain will be renewed after a few days. The size of the fluid-collecting element must be adapted to the size of the uterine volume. If necessary, the cervix is extended for access to the uterine cavity. The vacuum is also generated via an electronic pumping system. Negative pressures of −20 mm Hg to −200 mm Hg are used. Continuous suction is preferably used. Intermittent suction is applied. The intermittent suction can be modeled on a contraction rhythm. The same pressure patterns as described above can be used. The drain can be placed using endoscopic placement techniques.

Another indication exists in the perforation or rupture of the uterus. This involves a uterine wall defect. Using the intrauterine vacuum system, the defect can be sealed and contracted and glued.

BRIEF DESCRIPTION OF THE DRAWINGS

FIG. 1a is a top view of a device for intrauterine vacuum therapy according to a preferred embodiment.

FIG. 1b is a top view of a device for intrauterine vacuum therapy according to another preferred embodiment.

FIG. 2a is a longitudinal section view of the device shown in FIG. 1a.

FIG. 2b is a longitudinal section view of the device shown in FIG. 1b.

FIG. 3a is a cross-sectional view of the device shown in FIG. 1a.

FIG. 3b is a longitudinal section view of a device for intrauterine vacuum therapy according to another preferred embodiment.

FIG. 3c is a longitudinal section view of a device for intrauterine vacuum therapy according to another preferred embodiment.

FIG. 3d is a longitudinal section view of a device for intrauterine vacuum therapy according to another preferred embodiment.

FIG. 4 is a perspective view of a guide-rod and displaceable sheath according to a preferred embodiment of a device for intrauterine vacuum therapy.

FIG. 5 is a longitudinal section view of the female abdomen with a preferred embodiment of a device for intrauterine vacuum therapy in place prior to applying vacuum.

DETAILED DESCRIPTION OF PREFERRED EMBODIMENT

Figure 7A:
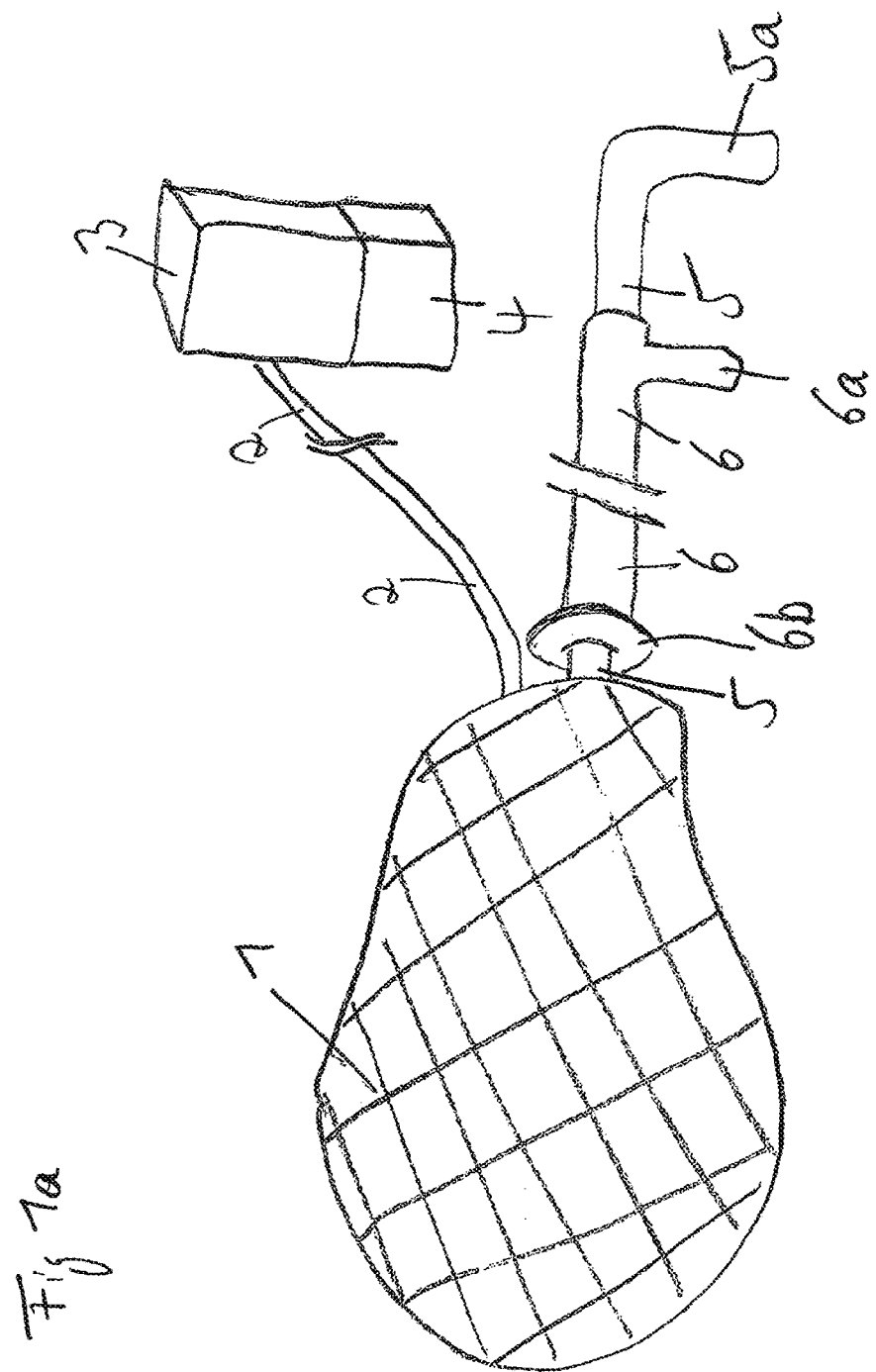
FIG. 7 is a representation of a negative pressure pattern showing a preferred pattern modeled on uterine contractions.

Hereinafter, the invention is explained based on figures, which illustrate embodiments.

FIG. 1a is a top view of fluid-collecting element (1) in a merely suggested pear-shape. It is fluid-conductively connected to a tubular fluid-communicating element (2), which is fluid-conductively connected to a secretion collection vessel (3) having a vacuum generating pump (4). Into the collection element (1), a guide-rod (5) with handle (5a) is introduced, which is situated in a sheath (6) that is movable on it, the latter is also at the proximal end with a grip (6a) and ends at the distal end in a disc-like plate (6b) for pushing the fluid-collecting element (1) forward.

FIG. 1b, like Figure, 1 is a top view of fluid-collecting element (1) in a merely suggested pear shape. It is fluid-conductively connected to a tubular fluid-communicating element (2), which is fluid-conductively connected to a secretion collection vessel (3) having a vacuum-generating pump (4). In collection element (1), an endoscope (11) is passed through. Endoscope (11) enters fluid-collecting element (1) in an inlet opening (1b) and exits in an outlet opening (1c). Endoscope (11) is located in a sheath (6), which is movable on it; the latter at the proximal end also has a handle (6a) and ends at the distal end in a disc-like plate (6b) for pushing fluid-collecting element (1) forward. The collecting element is movable on endoscope (11).

FIG. 2a is a longitudinal section view of FIG. 1a. Fluid-collecting element (1) in a merely suggested pear-shape is connected to tubular fluid-communicating element (2). At the distal end, the fluid-communicating element is equipped with lateral perforations (2a). Fluid-communicating element (2) is fluid-conductively connected to a secretion collection vessel (3) of a vacuum generating pump (4). In collection element (1), a cylindrical recesses (1a) in a longitudinal direction exists, into these, a guide-rod (5) with a handle (5a) is introduced and is located in a sheath (6) that is movable on it; the latter at the proximal end also has a handle (6a) and ends at the distal end in a disc-like plate (6b) for pushing fluid-collecting element (1) forward.

FIG. 2b is a longitudinal section view of FIG. 1b. Fluid-collecting element (1) having merely suggested pear-shape is connected to the tubular fluid-communicating element (2). At the distal end, the fluid-communicating element is equipped with lateral perforations (2a). Fluid-communicating element (2) is fluid-conductively connected to a secretion collection vessel (3) of a vacuum generating pump (4). In collector element (1), a cylinder-shaped recesses (1a) in a longitudinal direction exists, in these, an endoscope (11) is introduced in the inlet opening (1b) and exits through the outlet opening (1c). On endoscope (11), a sheath (6) that is movable on it, is at the proximal end (and) also provided with a handle (6) and ends at the distal end in a disc-like plate (6b) for pushing fluid-collection element (1) forward.

FIG. 3a is a cross-sectional view of FIG. 1a. The body of fluid-collecting element (1) with cylindrical recess (1a) can be seen. Into recess (1a), guide-rod (5) has been introduced. (2) is the tubular fluid-communicating element.

FIG. 3b is a longitudinal sectional view of a fluid collection body (1) with cylindrical cavity (1a) for a guide-rod. In fluid collection element (1) is a tubular fluid-communicating element (2) with perforations (2a). The fluid-communicating element is branched with several branch-like branches (2b).

FIG. 3c is a longitudinal sectional view of a fluid-collecting body (1) with a tubular fluid-communicating element (2) (with perforations 2a), which has T-piece-like branches (2c).

FIG. 3d is a longitudinal sectional view of a fluid-collecting body (1) with a tubular fluid-communicating element (2) (with perforations 2a) which rests in a loop (2d) in the fluid-collecting body. The fluid-collecting element enters and exits via openings (2e) and unites in y-shape (2f).

FIG. 4 is an illustration of guide-rod (5) with displaceable sheath (6). Guide-rod (5) has a handle (5a). The distal end of the sheath is closed off by a disc (6b). The distal end of guide-rod (5) is distended stamp-like (5b) to reduce perforation risks.

FIG. 5 shows a longitudinal section of the female abdomen. After childbirth, uterus (U) is large and heavily muscled. Through vagina (V), fluid-collection element (1) was introduced using guide-rod (5), which is curved and adapted to the natural course of the access path. The guide-rod has a handle (5a). Fluid-collection element (1) is fluid-conductively connected to tubular fluid-communicating element (2), which is connected to secretion collection vessel (3) and vacuum pump (4). As yet, no vacuum has been applied.

Figure 6:
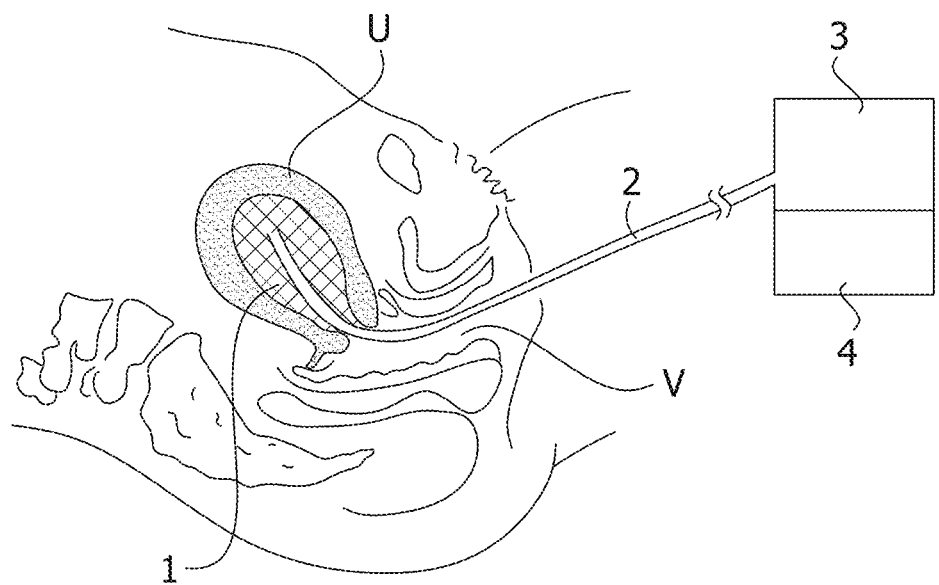
FIG. 6 is a longitudinal section view of the female abdomen with a preferred embodiment of a device for intrauterine vacuum therapy in place after applying vacuum.

FIG. 6, just like FIG. 5, shows a longitudinal section of the female abdomen. The guide-rod has been removed. Vacuum pump (4) generates a vacuum in secretion collection vessel (3). The latter is fluid-conductively connected to fluid-communicating element (2). The vacuum is transferred to fluid-collecting element (1). The inner wall of uterus (U) has been aspirated against fluid-collecting element (1), which collapses subject to the suction. After aspiration of uterus (U), using vacuum pump (3), specific vacuum pattern can be generated and transferred to the uterine wall. Vagina (V).

Figure 6A:
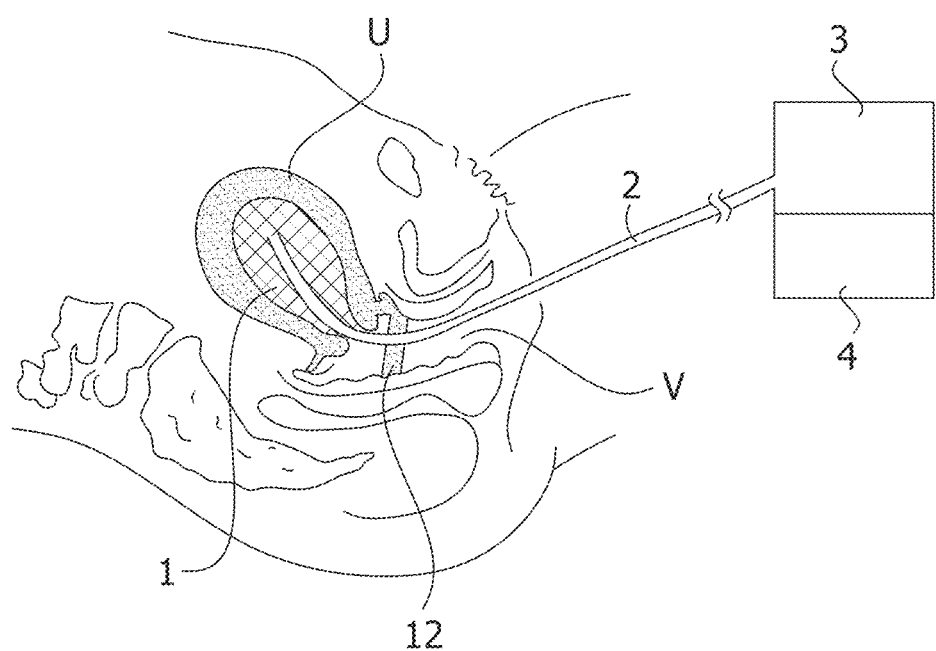
FIG. 6a is a longitudinal section view of the female abdomen with another preferred embodiment of a device for intrauterine vacuum therapy in place after applying vacuum.

FIG. 6a shows the same longitudinal section of the female abdomen as FIG. 6. In addition to FIG. 6, for better sealing, a pessary (12) has been introduced into the vagina. The guide-rod has been removed. Vacuum pump (4) generates a vacuum in secretion collection vessel (3). The latter is fluid-conductively connected to fluid-communicating element (2). The vacuum is transferred to fluid collection element (1). The inner wall of uterus (U) has been aspirated against fluid-collecting element (1), which collapses subject to the suction. After aspiration of uterus (U), using vacuum pump (3), specific vacuum pattern can be generated and transferred to the uterine wall. Vagina (V).

Figure 7:
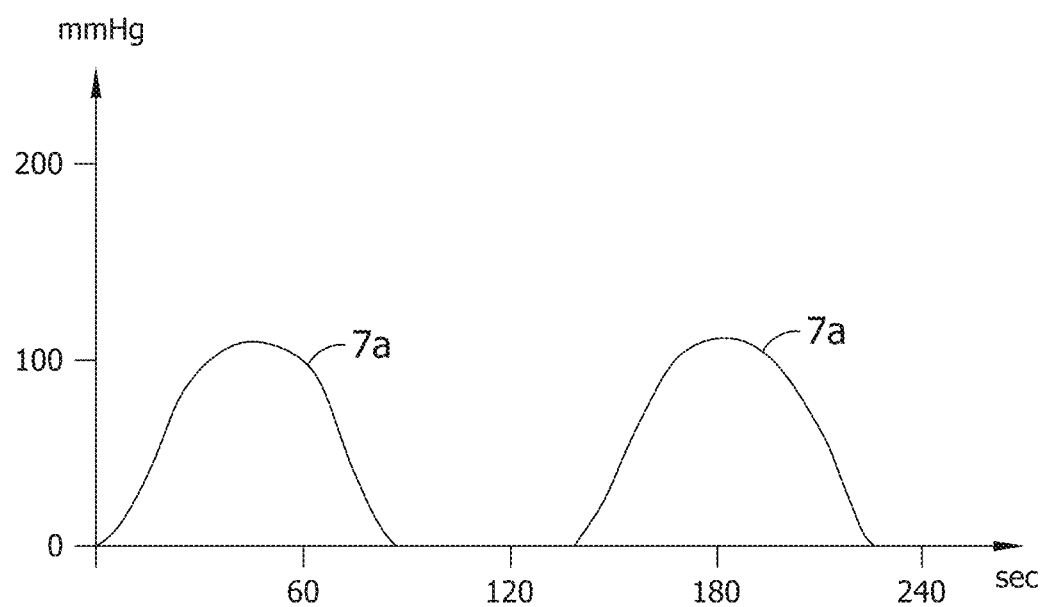

FIG. 7 is the representation of a negative pressure pattern showing a pattern modeled on uterine contractions, which can be generated using the vacuum pump. In this exemplary embodiment, the bell-shaped repeating negative pressure curve (7a) exists for approx. 90 s and pauses approx. 40 s. The maximum negative pressure is around −100 mmHg. During the pauses, no negative pressure is applied to the drain.

Figure 8:
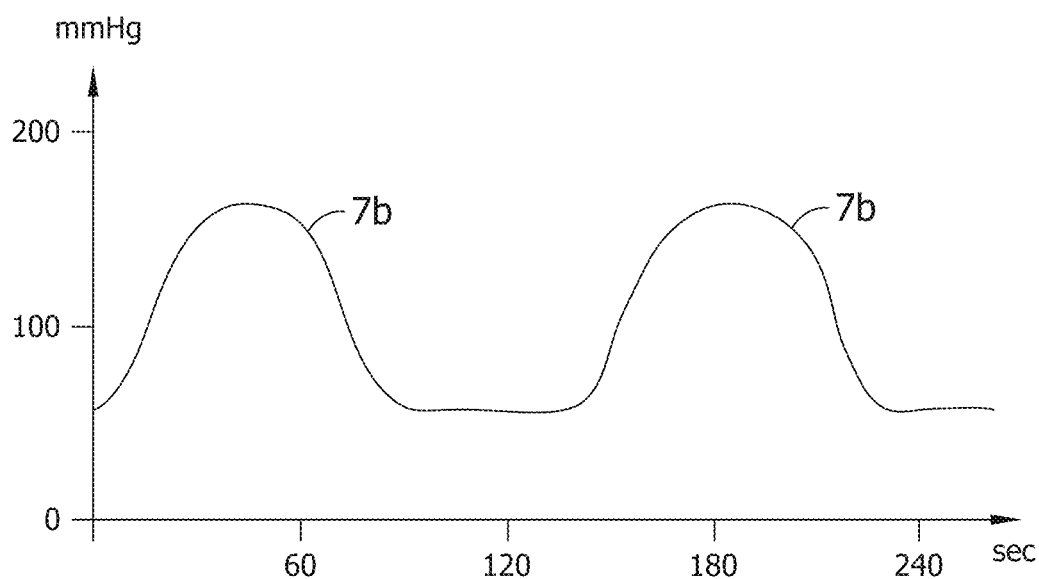
FIG. 8 is a representation of a negative pressure pattern showing another preferred pattern modeled on uterine contractions.

FIG. 8 is the representation of a negative pressure pattern showing a pattern modeled on uterine contractions, which can be generated using the vacuum pump. In this exemplary embodiment, the bell-shaped repeating negative pressure curve (7b) exists for approx. 90 s and pauses approx. 40 s. The maximum negative pressure is around −150 mmHg. The minimum negative pressure, whose plateau is not exceeded during the pauses and which is the base negative pressure, is around −50 mm Hg. This means that with this pattern a vacuum is always applied to the drain.

Figure 9:
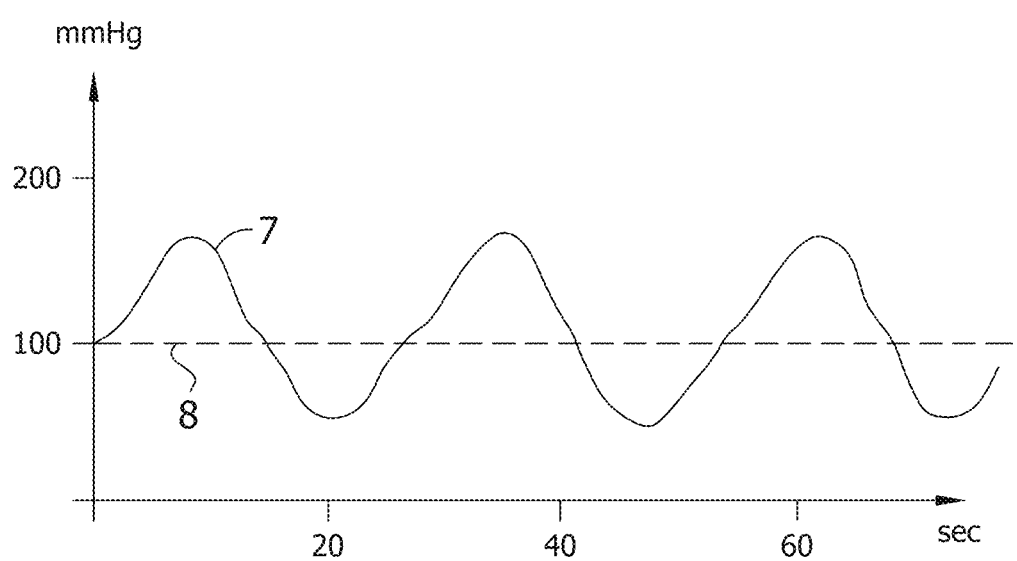
FIG. 9 is a representation of a negative pressure pattern showing a preferred undulating vacuum curve.

FIG. 9 is the representation of a negative pressure pattern with undulating vacuum curve (7), which can be generated using the vacuum pump. The highest and lowest negative pressures fluctuate around a mean negative pressure (8) of 100 mm Hg in this exemplary embodiment.

Figure 10:
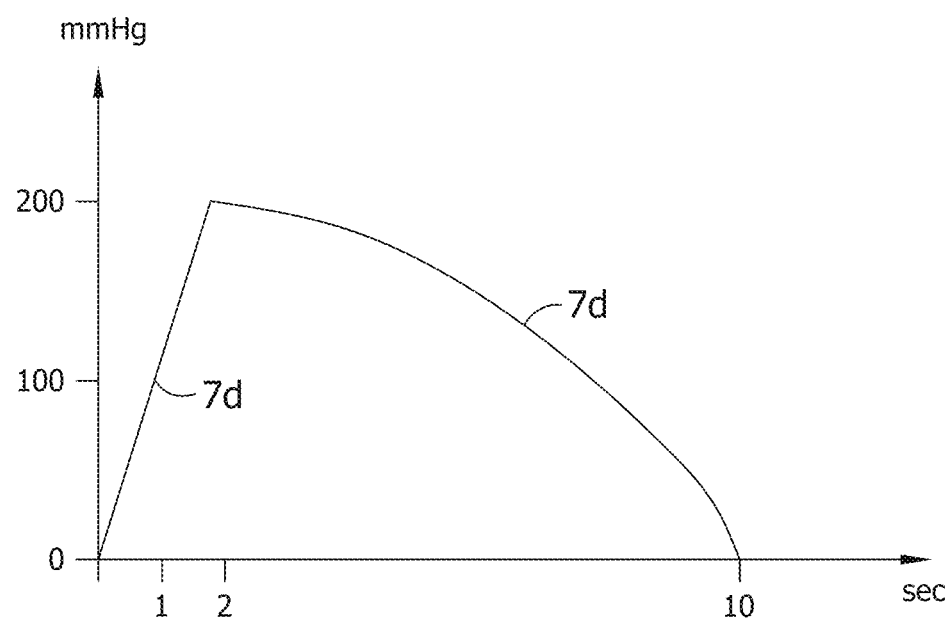
FIG. 10 is a representation of a negative pressure pattern showing a preferred sawtooth-like negative pressure curve.

FIG. 10 is the representation of a sawtooth-like negative pressure curve (7d), which can be generated using the vacuum pump. Within 2 s, a negative pressure of 200 mmHg is generated; thereafter, the negative pressure drops to 0 mmHg within 8 s.

Figure 11:
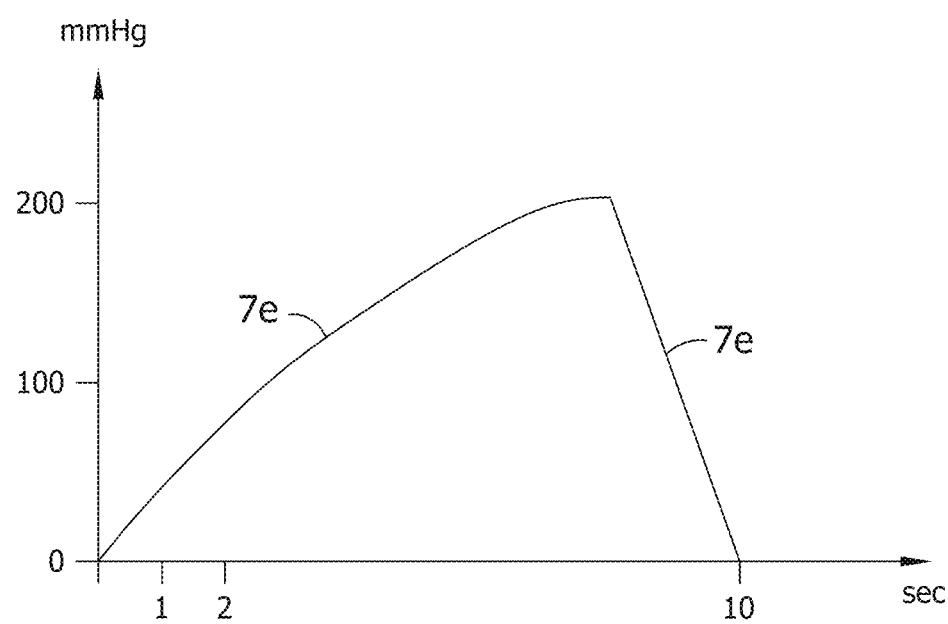
FIG. 11 is a representation of a negative pressure pattern showing another preferred sawtooth-like negative pressure curve.

FIG. 11 is the representation of a sawtooth-like negative pressure curve (7e), which can be generated using the vacuum pump. Within 8 s, a negative pressure of 200 mmHg is generated; thereafter, the negative pressure drops to 0 mmHg within 2 s.

Figure 12:
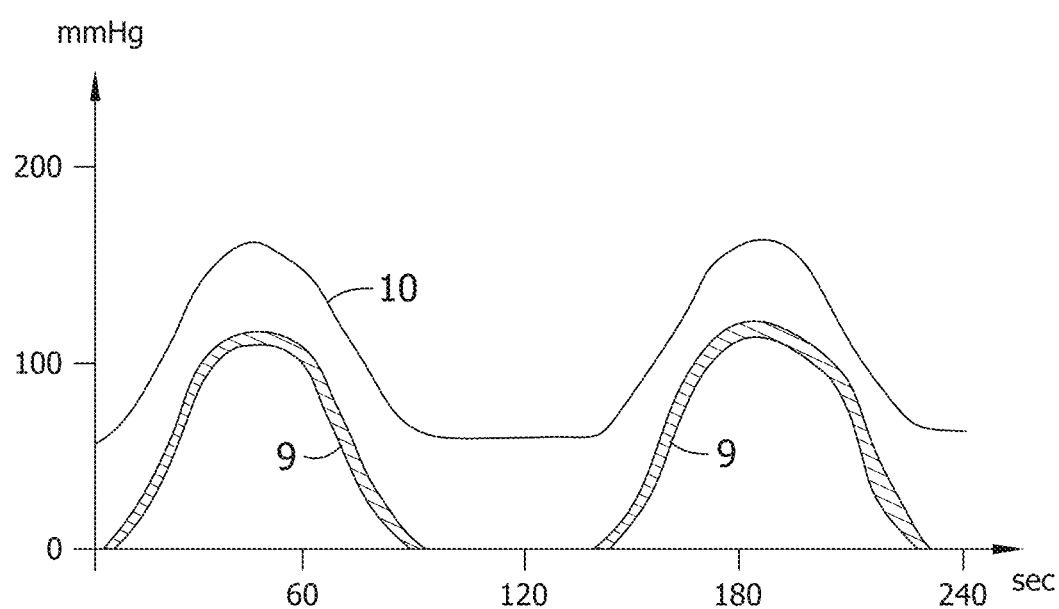
FIG. 12 is a representation of a negative pressure pattern showing a uterine contraction-like negative pressure curve synchronized with derived uterine contraction activity.

FIG. 12 is the representation of a uterine contraction-like negative pressure curve (10) with a plateau in the uterine contraction pause at −50 mm Hg and a maximum negative pressure of −150. This negative pressure curve is synchronized with the derived uterine contraction activity (9). The vacuum pump receives the signal of the uterine contraction activity (9) and synchronizes the negative pressure curve. The uterine contraction activity can be electromyographically discharged and transmitted to the pump as control signal.

The invention claimed is:

1. A device for intrauterine vacuum therapy comprising:
a fluid-collecting element defining an inlet opening at a proximal end and a tubular cavity for receiving a removable guide-rod during transvaginal insertion into a uterine cavity;
a fluid-communicating element having a perforated distal end fixed within the fluid-collecting element outside the tubular cavity and having a proximal end adapted for connection to a vacuum-generating system;
the guide-rod; and
a pusher sheath displaceable on the guide-rod, and wherein the pusher sheath has a disc-like plate on the distal end of the pusher sheath, and/or is widened funnel-like at its distal end.

2. The device of claim 1 wherein the fluid-collecting element comprises an open-cell foam having a cell size between 100 μm and 2000 μm.

3. The device of claim 1 wherein the fluid-collecting element is equipped with a hemostatic medication.

4. The device of claim 1 further comprising an open-cell film on the surface of the fluid-collecting element.

5. The device of claim 4 further comprising an additional fluid communicating element, wherein the additional fluid-communicating element is capable of delivering a hemostatic medication to the open-cell film.

6. The device of claim 1 wherein the fluid-collecting element has a compression stability between 10% and 90% when subject to a negative pressure between 20 mmHg and 200 mmHg.

7. The device of claim 1 wherein the distal end of the fluid-communicating element comprises a multiplicity of branches.

8. The device of claim 1 wherein the distal end of the fluid-communicating element is a loop.

9. The device of claim 1 further comprising a pessary disposed on the fluid-communicating element.

10. A system for intrauterine vacuum therapy comprising:
the device of claim 1;
and
a vacuum pump capable of applying a negative pressure to the device.

11. A method of treating an intrauterine wound or infection, the method comprising:
providing the device of claim 1;
using the guide-rod to transvaginally insert the device into the uterine cavity;
connecting a vacuum pump to the proximal end of the device; and
using the vacuum pump to apply a negative pressure to the device, wherein the uterus collapses and the inner wall is aspirated against the device.

12. The method of claim 10 wherein the device further comprises an open-cell film on the surface of the fluid-collecting element and the method further comprises introducing a hemostatic medication in a targeted manner to an inner wound surface via the open-cell film.

13. The method of claim 11 wherein the device further comprises an additional fluid communicating element and the method further comprises delivering a hemostatic medication to the open-cell film via the additional fluid-communicating element.

14. The method of claim 10 wherein the fluid-collecting element further defines an outlet opening at the distal end and wherein the tubular cavity extends over the entire longitudinal axis of the fluid-collecting element, the method further comprising pushing the fluid-collecting element into the uterine cavity using the pusher sheath.

15. The method of claim 10 wherein the vacuum pump generates a negative pressure in a suction pattern.

16. The method of claim 14 wherein the suction pattern comprises applying an increasing negative pressure to the drain up to a maximum of about 100 mmHg and decreasing the negative pressure down to 0 mmHg over about 90 seconds and applying no negative pressure to the drain for about 40 seconds.

17. The method of claim 14 wherein the suction pattern comprises applying an increasing negative pressure to the drain up to a maximum of about 150 mmHg and decreasing the negative pressure down to about 50 mmHg over about 90 seconds and applying a negative pressure of about 50 mmHg to the drain for about 40 seconds.

18. The method of claim 14 wherein the suction pattern comprises applying a fluctuating negative pressure having a mean of 100 mmHg to the drain.

19. The method of claim 14 wherein the suction pattern comprises generating a negative pressure of about 200 mmHg within about 2 seconds and dropping the negative pressure to 0 mmHg within about 8 seconds.

20. The method of claim 14 wherein the suction pattern comprises generating a negative pressure of about 200 mmHg within about 8 seconds and dropping the negative pressure to 0 mmHg within about 2 seconds.

21. The method of claim 10 further comprising monitoring uterine contraction activity and synchronizing the suction pattern with the uterine contraction activity.

22. The device of claim 1 wherein the fluid-collecting element is pear-shaped.

23. The device of claim 1, wherein the tubular cavity terminates in a blind end.

\* \* \* \* \*